US008388668B2

(12) United States Patent  
Peyman

(10) Patent No.: US 8,388,668 B2  
(45) Date of Patent: Mar. 5, 2013

(54) METHODS TO REGULATE POLARIZATION OF EXCITABLE CELLS

(75) Inventor: Gholam A. Peyman, New Orleans, LA (US)

(73) Assignee: Gholam A. Peyman, Sun City, AZ (US)

( * ) Notice: Subject to any disclaimer, the term of this patent is extended or adjusted under 35 U.S.C. 154(b) by 1482 days.

(21) Appl. No.: 11/197,869

(22) Filed: Aug. 5, 2005

(65) Prior Publication Data

US 2007/0028928 A1 Feb. 8, 2007

(51) Int. Cl.
*A61N 5/06* (2006.01)
(52) U.S. Cl. ............. 607/88; 607/94; 977/904; 977/925
(58) Field of Classification Search .......... 607/1, 88–94; 604/20; 257/40, 439, 449
See application file for complete search history.

(56) References Cited

U.S. PATENT DOCUMENTS

| 5,220,181 | A  | * | 6/1993  | Kanai et al. ................... 257/40  |
| 6,566,595 | B2 | * | 5/2003  | Suzuki ........................... 257/431 |
| 6,641,553 | B1 |   | 11/2003 | Chee et al. ...................... 604/68  |
| 2003/0022374 | A1 | * | 1/2003 | Greenbaum et al. .......... 435/455 |

OTHER PUBLICATIONS

Greenbaum et al, "Application of Photosynthesis to Artificial Sight" paper presented at the Nanoscale Science and Technology in Medicine Symposium, 23rd International Conference of the IEEE Engineering in Medicine and Biology Society, Oct. 25-28, 2001, Istambul Turkey.*
Anscombe, *Quantum Dots: Small Structures Poised to Break Big*, Photonics Spectra, Jul. 2005, pp. 94-96.
Curtin, *Nano Photovoltaic/Solar Cells*, U.S. Published Application No. 2004/0003839, published Jan. 8, 2004, U.S. Appl. No. 10/357,460, filed Feb. 4, 2003.
Chow et al., *Methods for Improving Damaged Retinal Cell Function*, U.S. Published Application No. 2003/0014089, published Jan. 16, 2003, U.S. Appl. No. 10/056,793, filed Jan. 23, 2002.
Chow, *Treatment of Degenerative Retinal Disease via Electrical Stimulation of Surface Structures*, U.S. Published Application No. 2005/0004625, published Jan. 6, 2005, U.S. Appl. No. 10/863,519, filed Jun. 9, 2004.
Mali et al., *Intravitreous Injection of a Membrane Depolarization Agent Causes Retinal Degeneration Via Matrix Metalloproteinase-9*, Investigative Ophthalmology and Visual Science, 2005; 46:2125-2132.

* cited by examiner

*Primary Examiner* — Lee S Cohen
(74) *Attorney, Agent, or Firm* — Thompson Hine LLP

(57) ABSTRACT

Minimally invasive delivery with intercellular and/or intracellular localization of nano- and micro-particle solar cells within and among excitable biological cells to controllably regulate membrane polarization of such cells. The cells include retinal and other sensory cells, muscle cells, and nerve cells.

12 Claims, 2 Drawing Sheets

METHODS TO REGULATE POLARIZATION OF EXCITABLE CELLS

FIELD OF THE INVENTION

The invention relates to methods to regulate polarization of excitable cells.

BACKGROUND

Mechanisms to correct, reduce, and/or prevent physiological electro-sensory damage, e.g., in the brain, in the eye, etc., are desirable.

DETAILED DESCRIPTION

Figure 1:
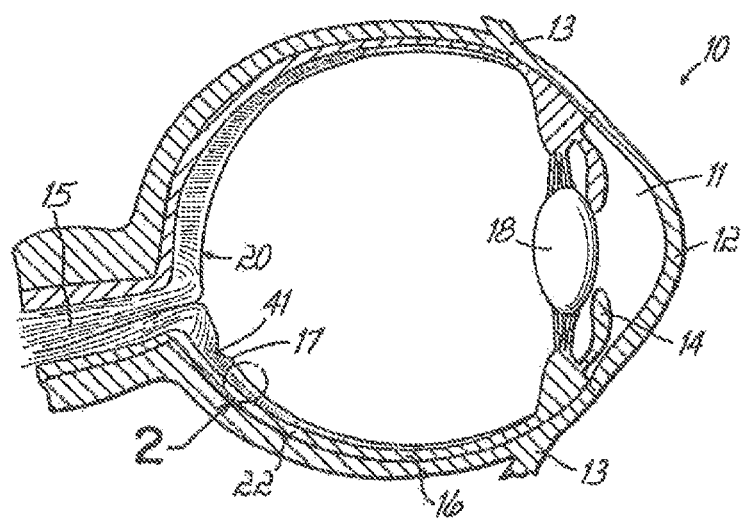
FIG. 1 is a drawing of a longitudinal section of a human eye.

Delivery and intercellular and/or intracellular localization of nano- and micro-particle solar cells within and/or among excitable biological cells to regulate membrane polarization of biological cells. The inventive method provides solar cells in a minimally invasive procedure; the solar cells are not implanted in the body in an invasive procedure. The inventive method provides a plurality of solar cells as discrete individual particles; the solar cells are not connected as a unit and do not have a backing layer or backing material. The inventive method uses solar cells that may be activated by ambient light; the method does not use an electrical apparatus and thus does not use photodiodes, stimulating electrodes, or other electrical devices. The inventive method uses solar cells to enhance the regulation of polarization by the excitable biological cells themselves; the solar cells facilitate or boost the ability of excitable biological cells to normalize or regulate their own polarity. The inventive method provides for excitable biological cells to regulate their own polarity; stimulation of the solar cells used in the invention does not generate an action potential to regulate polarity, but instead facilitates the biological cells themselves to regulate polarity.

Biological cells are bound by a plasma membrane. In all cells, this membrane has a resting potential. The resting potential is an electrical charge across the plasma membrane of the non-excited or resting cell, rendering the interior of the cell negative with respect to the exterior. Hence, the plasma membrane of all biological cells in their resting state is polarized.

The extent of the resting potential varies among different cell types. In cells such as nerve, muscle, and retinal cells, which are excitable in that they can be stimulated to create an electric current, the resting potential is about −70 millivolts (mv). This resting potential arises from two components of the plasma membrane: the sodium/potassium ATPase, which pumps two potassium ions ($K^+$) into the cell for every three sodium ions ($Na^+$) it pumps out of the cell, and "leakiness" of some $K^+$ channels, allowing slow facilitated diffusion of $K^+$ out of the cell. The result is a net loss of positive charge from within the resting cell.

Certain external stimuli reduce the charge across the plasma membrane, resulting in membrane depolarization. As one example, mechanical stimuli (e.g., stretching, sound waves) activate mechanically-gated $Na^+$ channels. As another example, certain neurotransmitters (e.g., acetylcholine) open ligand-gated $Na^+$ channels. In each case, the facilitated diffusion of $Na^+$ into the cell depolarizes the membrane; it reduces the resting potential at that membrane location. This creates an excitatory postsynaptic potential (EPSP).

If the potential at any membrane location is reduced to the threshold voltage, many voltage-gated $Na^+$ channels open in that location, generating an influx of $Na^+$. This localized, sudden, complete depolarization opens adjacent voltage-gated $Na^+$ channels. The result is a wave of depolarization along the cell membrane, referred to as the action potential or, in excitable cells, an impulse.

A second stimulus applied to an excitable cell within a short time (less than 0.001 second) after the first stimulus will not trigger another impulse. This is because the membrane is depolarized, leaving the cell in a refractory period. Only when the −70 mv polarity is reestablished, termed repolarization, will an excitable cell be able to respond to another stimulus. Repolarization is established by facilitated diffusion of $K^+$ out of the cell. When the cell is finally rested, $Na^+$ that entered the cell at each impulse are actively transported back out of the cell.

Hyperpolarization occurs when negatively charged chloride ions ($Cl^-$) enter the cell and $K^+$ exit the cell. Some neurotransmitters may facilitate this by opening $Cl^-$ and/or $K^+$ channels in the plasma membrane. Hyperpolarization results in an inhibitory postsynaptic potential (IPSP); although the threshold voltage of the cell is unchanged, it requires a stronger excitatory stimulus to reach threshold.

Abnormal cell polarization may affect regenerative and/or functional process of excitable cells, and result in cell dysfunction. Abnormal cell polarization includes, but is not limited to, any of the following and whether transient or sustained: loss of polarization, decreased polarization, altered polarization, hyperpolarization, and any deviation from normal cell polarization. Excitable cells include, but are not limited to, sensory cells (e.g., retina and macula of the eye), neuronal cells in the central nervous system (CNS) (brain and spinal cord) and peripheral nervous system, muscle cells (striated, cardiac, and smooth muscle cells).

The orientation of the cell with respect to its apical, lateral, and basal surfaces may affect polarization and may be regulated by the inventive method. Adjacent cells communicate in the lateral domain, with attachment or contact sites by which cells adhere to one another. Terminal bars, attachment sites between cells that act as a barrier to passage of substances, are located around the entire circumference of cells and are composed of junctional complexes responsible for joining individual cells. Occluding junctions, also referred to as tight junctions or zonula occludentes, are located apically within the lateral domain and encircle the cell, separating the luminal region from the intercellular space and cytoplasm. These are narrow regions of contact between the plasma membranes of adjacent cells and seal off the intercellular space, forming an impermeable diffusion barrier between cells and preventing proteins from migrating between apical and lateral surfaces of the cell. In one embodiment, the method selectively regulates polarization in areas of the cell bound by occluding junctions. Particles may be selectively positioned and/or selectively regulated to regulate polarization at a desired site.

Ischemic cell death is caused by failure of the ionic pumps of the plasma membrane. Depolarization of the plasma membrane in retinal cells and subsequent synaptic release of L-glutamate are implicated in ischemic retinal damage. Mali et al. (Investigative Ophthalmology and Visual Science, 2005, 46, 2125) reported that when KCl, a known membrane depolarizing agent, is injected into the vitreous humor, the subsequent membrane depolarization results in a dose- and time-related upregulation of matrix metalloproteinase (MMP)-9 activity and protein in the retina. This was associated with an increase in proapoptotic protein Bax and apoptotic death of cells in the ganglion cell layer and inner nuclear layer, and subsequent loss of NF-L-positive ganglion cells and calretinin-positive amacrine cells. A synthetic MMP inhibitor inhibited KCl-mediated MMP-9 upregulation, which led to a significant attenuation of KCl-induced retinal damage. Regulating polarization thus inhibits MMP-9 and decreases damage that can diminish visual acuity.

Methods to regulate membrane polarization of excitable cells assist in minimizing physiologic damage and reducing pathology including but not limited to ischemic damage to the retina, degenerative diseases of the retina including but not limited to retinitis pigmentosa, ischemic and/or degenerative diseases of cardiac muscle, and/or ischemic and degenerative diseases of cerebral tissue, etc. In turn, the method minimizes or prevents undesirable effects such as loss of visual acuity, myocardial infarction, cerebral stroke, etc. and enhances a patient's quality of life.

The inventive method may be more fully appreciated with respect to its utility in a single organ, such as the eye. One skilled in the art will realize, however, that it is not so limited and is applicable to other excitable cells.

FIG. 1 shows a mammalian eye 10. The structures and locations of the anterior chamber 11, cornea 12, conjunctiva 13, iris 14, optic nerve 15, sclera 16, macula lutea or macula 17, lens 18, retina 20, choroid 22, and fovea 41 are indicated. The macula is located in the center of the posterior part of the retina 20 and is the most sensitive portion of the retina. It is an oval region of about 3 mm by 5 mm, in the center of which is a depression, the fovea centralis 41, from which rods are absent. Inside the fovea 41 is the point of entrance of the optic nerve 15 and its central artery. At this point, the retina 20 is incomplete and forms the blind spot.

Figure 2:
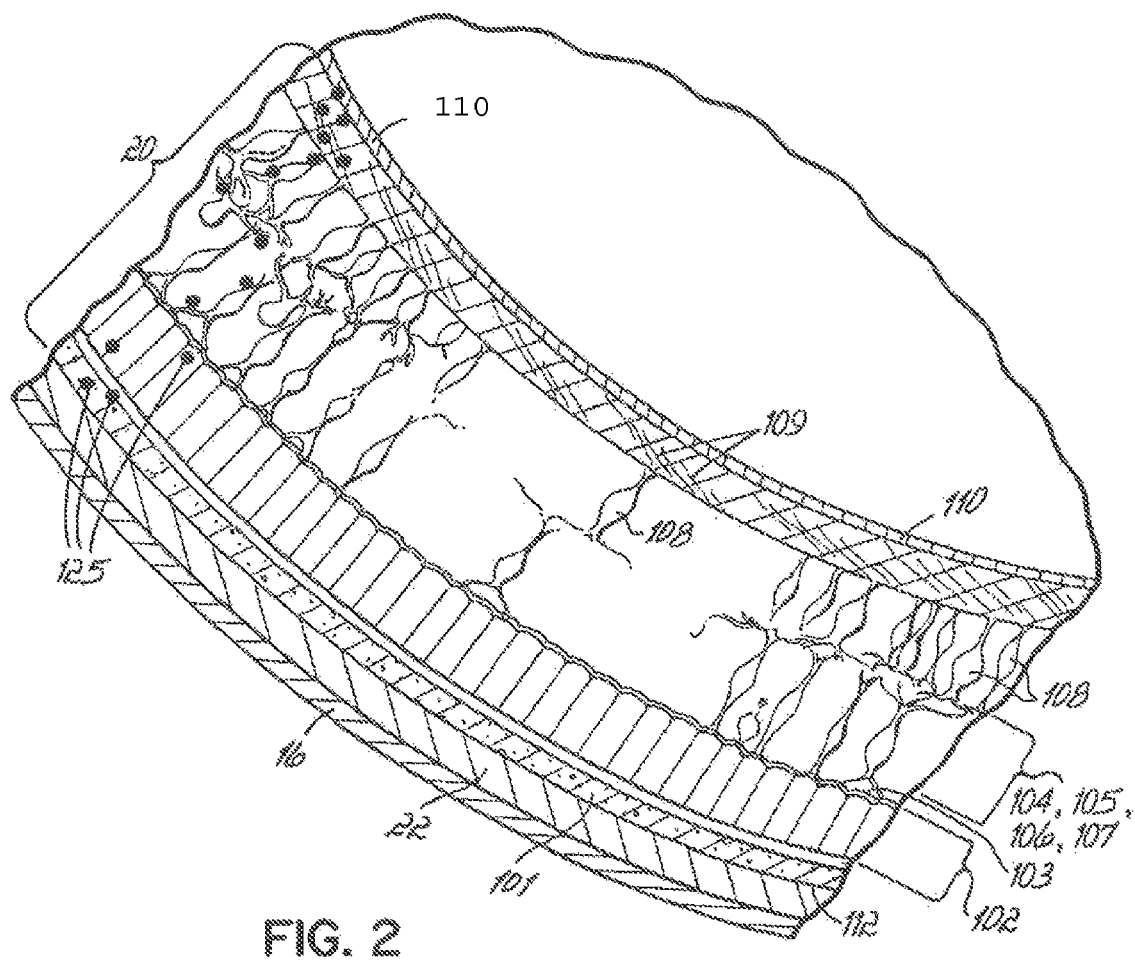
FIG. 2 is an enlarged diagrammatic illustration of the circled area 2 of FIG. 1 showing detailed retinal structures.

The encircled area 2 of FIG. 1 is shown in exploded form in FIG. 2. As shown in FIG. 2, the retina 20 forms the innermost layer of the posterior portion of the eye and is the photoreceptor organ. The retina 20 has an optical portion that lines the inner surface of the choroid 22 and extends from the papilla of the optic nerve 15 to the ora serrata 21 anteriorly. At the papilla, where the retina 20 stops, and at the ora serrata 21, the retina 20 is firmly connected with the retinal pigment epithelium (RPE) 101.

The retina 20 has ten parallel layers. These are, from the choroid in, as follows: the RPE 101, photoreceptor cells (rod and cone inner and outer segments) 102, the external limiting membrane 103, the outer nuclear layer 104, the outer plexiform layer 105, the inner nuclear layer 106, the inner plexiform layer 107, the layer of ganglion cells 108, the layer of optic nerve fibers or neurofiber layer 109, and the internal limiting membrane 110. The internal limiting membrane 110 is very thin (less than 5 μm), and normally adheres with the neurofiber layer 109 of the ganglion cells 108.

The pigment epithelial cell layer or RPE 101 rests on a basal lamina termed Bruch's membrane 112 that is adjacent to the choroid 22.

The next three layers are composed of various portions of one cell type, termed the first neuron. These layers are the photoreceptor region (lamina) 102 of rods and cones, the external limiting membrane 103, and the outer nuclear layer 104 composed of the nuclei of the rods and cones cells. The rods have long, thin bodies, and the cones have a broad base. The rods have greater sensitivity for low light levels; the cones have better visual acuity in daylight and are also responsible for color perception. There are three types of cones, each absorbing light from a different portion of the visible spectrum: long-wavelength (red), mid-wavelength (green), and short-wavelength (blue) light. Both rods and cones contain the transmembrane protein opsin, and the prosthetic group retinal, a vitamin A derivative. The opsins in each cell type contain different amino acids that confer differences in light absorption.

The RPE, photoreceptor cells, external limiting membrane, outer nuclear layer, and outer plexiform layer constitute the neuro-epithelial layer of the retina.

The inner nuclear layer, inner plexiform layer, ganglion cell layer, nerve fiber layer, and internal limiting membrane constitute the cerebral layer of the retina. The inner nuclear layer contains bipolar cells, ganglion cells, horizontal cells, amacrine cells, Muller cells, and astrocytes, the latter two being types of glial cells. The Muller cells have nuclei in the inner nuclear area and cytoplasm extending from the internal limiting membrane 110 to the external limiting membrane 103. The external limiting membrane 103 is a region of terminal bars between Muller's cells and the visual receptors.

The next three layers of the retina are composed of various parts of the second neurons, whose nuclei reside in the inner nuclear layer and whose cytoplasmic processes extend into the outer plexiform layer to synapse with the receptor cells and to the inner plexiform layer to synapse with the ganglion cells. Thus, the second neuron is bipolar.

The third neuron, the multipolar ganglion cells, sends its nerve fiber (axon) to the optic nerve.

The last layer of the retina is the internal limiting membrane (ILM) on which the processes of the Muller's cells rest.

The retina contains a complex interneuronal array. Bipolar cells and ganglion cells are sensory cells that together form a path from the rods and cones to the brain. Other neurons form synapses with the bipolar cells and ganglion cells and modify their activity. For example, ganglion cells, or ganglia, generate action potentials and conduct these impulses back to the brain along the optic nerve. Vision is based on the modulation of these impulses, but does not require the direct relationship between a visual stimulus and an action potential. The visual photosensitive cells, the rods and cones, do not generate action potentials, as do other sensory cells (e.g., olfactory, gustatory, and auditory sensory cells).

Muller cells, the principal type of glial cells, form architectural support structures stretching radially across the thickness of the retina, and forming the limits of the retina at the outer and inner limiting membranes, respectively. Muller cell bodies in the inner nuclear layer project irregularly thick and thin processes in either direction to the outer and inner limiting membranes. These processes insinuate themselves between cell bodies of the neurons in the nuclear layers, and envelope groups of neural processes in the plexiform layers. Retinal neural processes can only have direct contact, without enveloping Muller cell processes, at their synapses. The junctions forming the outer limiting membrane are between Muller cells, and other Muller cells and photoreceptor cells, as sturdy desmosomes or zonula adherens. Muller cells perform a range of functions that contribute to the health of the retinal neurons. These functions include supplying endproducts of anaerobic metabolism (breakdown of glycogen) to fuel neuronal aerobic metabolism; removing neural waste products such as carbon dioxide and ammonia and recycling spent amino acid transmitters; protecting neurons from exposure to excess neurotransmitters using uptake and recycling mechanisms; phagocytosis of neuronal debris and release of neuroactive substances; synthesizing retinoic acid, required in the development of the eye and nervous system, from retinol; controlling homeostasis and protecting neurons from deleterious changes in their ionic environment by taking up and redistributing extracellular $K^+$; and contributing to generation of the electroretinogram (ERG) b-wave, the slow P3 component of the ERG, and the scotopic threshold response (STR) by regulating $K^+$ distribution across the retinal vitreous border, across the whole retina, and locally in the inner plexiform layer of the retina.

Astrocytes, the other type of glial cell, envelope ganglion cell axons and have a relationship to blood vessels of the nerve fiber, suggesting they are axonal and vascular glial sheaths and part of a blood-brain barrier. They contain abundant glycogen, similar to Muller cells, and provide nutrition to the neurons in the form of glucose. They may serve a role in ionic homeostasis in regulating extracellular $K^+$ levels and neurotransmitter metabolism. They have a characteristic flattened cell body and fibrous radiating processes which contain intermediate filaments. The cell bodies and processes are almost entirely restricted to the nerve fiber layer of the retina. Their morphology changes from the optic nerve head to the periphery: from extremely elongated near the optic nerve to a symmetrical stellate form in the far peripheral retina.

Microglial cells are not neuroglial cells and enter the retina coincident with mesenchymal precursors of retinal blood vessels in development, and are found in every layer of the retina. They are one of two types. One type is thought to enter the retina at earlier stages of development from the optic nerve mesenchyme and lie dormant in the retinal layers for much of the life of the retina. The other type appears to be blood-borne cells, possibly originating from vessel pericytes. Both types can be stimulated into a macrophagic function upon retinal trauma, in degenerative diseases of the retina, etc. when they then engage in phagocytosis of degenerating retinal neurons.

All glial cells in the central nervous system (CNS) are coupled extensively by gap junctions. This coupling underlies several glial cell processes, including regulating extracellular $K^+$ by spatial buffering, propagating intercellular $Ca^{2+}$ waves, regulating intracellular ion levels, and modulating neuronal activity.

Activation of retinal glial cells with chemical, mechanical, or electrical stimuli often initiate propagated waves of calcium ions ($Ca^{2+}$). These $Ca^{2+}$ waves travel at a velocity of 23 μm/second and up to 180 μm/second from the site of initiation. The waves travel through both astrocytes and Muller cells, even when the wave is initiated by stimulating a single astrocyte.

$Ca^{2+}$ waves propagate between glial cells in the retina by two mechanisms: diffusion of an intracellular messenger through gap junctions, and release of an extracellular messenger. $Ca^{2+}$ wave propagation between astrocytes is mediated largely by diffusion of an intracellular messenger, likely inositol triphosphate (IP3), through gap junctions, along with release of adenosine triphosphate (ATP). Propagation from astrocytes to Muller cells, and from one Muller cell to other Muller cells, is mediated by ATP release.

Retinal neurons and glial cells also communicate. Muller cells have transient $Ca^{2+}$ increases that occur at a low frequency. Stimulating the retina with repetitive light flashes significantly increases the frequency of these $Ca^{2+}$ transients, most prominent in Muller cell endfeet at the retinal surface, but also in Muller cell processes in the inner plexiform layer. This neuron-to-glial cell communication indicates that glial cell $Ca^{2+}$ transients are physiological responses in vivo.

Stimulated glial cells directly modulate the electrical activity of retinal neurons, leading either to enhanced or depressed neuronal spiking. Inhibitory glial modulation of neuronal spiking may be $Ca^{2+}$-dependent, because the magnitude of neuronal modulation was proportional to the amplitude of the $Ca^{2+}$ increase in neighboring glial cells. Glial cells can modulate neuronal activity in the retina by at least three mechanisms. In some ganglion cells, glial cell activation facilitates synaptic transmissions and enhances light-evoked spiking. In other ganglion cells, there is depressed synaptic transmissions and decreased spiking. Glial cell activation can also result in ganglion cells hyperpolarization, mediated by activating Al receptors and opening neuronal $K^+$ channels.

Stimulated glial cells also indirectly modulate the electrical activity of retinal neurons. This is mediated by glutamate uptake by Muller cells at synapses by glutamate transporters such as GLAST (EAAT1) and GLT-1 (EAAT2) in Muller cells. When glutamate transport in the retina is blocked, both the amplitude and the duration of ganglion cell EPSCs are increased. Glial cell modulation of electrical activation of retinal neurons is also mediated by regulating extracellular $K^+$ and $H^+$ levels. Neuronal activity leads to substantial variations in the concentration of $K^+$ and $H^+$ in the extracellular space, which can alter synaptic transmission; an increase of $K^+$ depolarizes synaptic terminals, while an increase of $H^+$ blocks presynaptic $Ca^{2+}$ channels and NMDA receptors. Muller cells regulate extracellular concentrations of $K^+$ and $H^+$, thus influencing the effect of these ions on synaptic transmission.

With reference to FIG. 2, one skilled in the art will appreciate that solar cell micro- and/or nano-particles 125, provided selectively or substantially throughout the all regions of the retina, enhance, facilitate or boost the ability of these biological cells to regulate their polarity. This is in contrast to use of a device that supplies an electrical potential, that is implanted in an invasive surgical procedure, that is localized, etc.

Besides pathologies in one or more of the above described mechanisms to maintain and/or regulate retinal cell polarity, other excitable cells besides the retina may have pathologies that occur from defects in cell plasma membrane polarization. As one example, excitable cells in the brain of Alzheimer's patients have abnormal electrical conducting and stabilizing mechanisms, resulting in loss of electrical stimulation. Repolarization of these cells provides additional stimulation to replace the abnormal cell membrane polarization and/or the cell membrane polarization that was diminished or lost. As another example, glial cell scar tissue culminating from epileptic seizures results in abnormal electrical stabilizing mechanisms in excitable cells of the brain. Repolarization of these cells provides a stabilized threshold, resulting in a calming effect. One skilled in the art will appreciate other pathologies for which the inventive method may be used.

The inventive method includes mechanisms to delay, minimize, reduce, alleviate, correct, or prevent electro-sensory polarization pathologies. Such mechanisms may attenuate cellular damage resulting from abnormal polarization, reduced polarization, enhanced polarization, hyperpolarization, or loss of polarization. These polarization defects may be of any type and/or cell combination, and may stimulate and/or de-stimulate the cell(s). They may, for example, be transient in one cell type, sustained in one cell type, propagated to affect adjacent cells, propagated along a network to affect non-adjacent cells, etc.

One embodiment provides nano- or micro-sized solar cells to regulate the polarity of excitable cells. As previously described, excitable cells include, but are not limited to, sensory cells such as the retina of the eye, all three types of muscle cells, and central and peripheral system nerve cells. Such nano- or micro-sized solar cells are hereinafter generally referred to as particles 125 as shown in FIG. 2. Particles encompass any and all sizes which permit passage through intercellular and/or intracellular spaces in the organ or area of the organ of interest. For example, intercellular spaces in the retina are about 30 angstroms ($30 \times 10^{-8}$), so that particles for intercellular retinal distribution may be sized for these spaces, as known to one skilled in the art.

The solar cell nano- and/or micro-particles 125 are three dimensional semiconductor devices. The particles use light energy or ultrasound energy to generate electrical energy to provide a photovoltaic effect. In one embodiment, the particle material is a ceramic. In another embodiment, the particle material is a plastic. In another embodiment, the particle material is silicon. Particles of crystalline silicon may be monocrystalline cells, poly or multicrystalline cells, or ribbon silicon having a multicrystalline strucutre. These are fabricated as microscale or nanoscale particles that are administered to a patient.

While each solar cell particle is oriented, the plurality of particles provided in the body are not uniformly directionally oriented, nor do they require a backing layer to maintain orientation or position. They have a positive-negative (P-N) junction diode and may be constructed as either negative-intrinsic-positive (NIP) or positive-intrinsic-negative (PIN), as known to one skilled in the art.

As an example, p-type silicon wafers, and doped p-type silicon wafers to form n-type silicon wafers, are contacted to form a p-n junction. Electrons diffuse from the region of high electron concentration, the n-type side of the junction, into the region of low electron concentration, the p-type side of the junction. When the electrons diffuse across the p-n junction, they recombine with an electron deficiency (holes) on the p-type side. This diffusion of carriers does not happen indefinitely however, because of the electric field created by the imbalance of charge immediately either side of the junction which this diffusion creates. Electrons from donor atoms on the n-type side of the junction cross into the p-type side, leaving behind the (extra) positively charged nuclei of the group 15 (V) donor atoms such as phosphorous or arsenic, leaving an excess of positive charge on the n-type side of the junction. At the same time, these electrons are filling holes on the p-type side of the junction and are becoming involved in covalent bonds around the group 13 (III) acceptor atoms such as aluminum or gallium, making an excess of negative charge on the p-type side of the junction. This imbalance of charge across the p-n junction sets up an electric field which opposes further diffusion of charge carriers across the junction. The region where electrons have diffused across the junction is called the depletion region or the space charge region because it no longer contains any mobile charge carriers. The electric field which is set up across the p-n junction creates a diode, allowing current to flow in only one direction across the junction. Electrons may pass from the n-type side into the p-type side, and holes may pass from the p-type side to the n-type side. Because the sign pf the charge on electrons and holes is opposite, current flows in only one direction. Once the electron-hole pair has been created by the absorption of a photon, the electron and hole are both free to move off independently within a silicon lattice. If they are created within a minority carrier diffusion length of the junction, then, depending on which side of the junction the electron-hole pair is created, the electric field at the junction will either sweep the electron to the n-type side, or the hole to the p-type side.

One embodiment of the invention uses nanocrystals of semiconductor material referred to as quantum dots (Evident Technologies, Troy N.Y.). These have a composition and size that provides quantum properties between that of single molecules and bulk materials, and are tunable to absorb light over the spectrum from visible to infrared energies. Their dimensions are measured in nanometers, e.g., diameter between about 1 nm to about 100 nm. When combined with organic semiconductors selected to have the desired activation properties, they result in particles with selectable features.

Nanocrystals are semiconductors with tunable bandgaps. The quantum dot nanocrystal absorption spectrum appears as a series of overlapping peaks that get larger at shorter wavelengths. Because of their discrete electron energy levels, each peak corresponds to an energy transition between discrete electron-hole (exciton) energy levels. The quantum dots do not absorb light that has a wavelength longer than that of the first exciton peak, also referred to as the absorption onset. Like other optical and electronic properties, the wavelength of the first exciton peak, and all subsequent peaks, is a function of the composition and size of the quantum dot. Smaller dots result in a first exciton peak at shorter wavelengths.

The quantum dots may be provided as a core, with a shell or coating of one or more atomic layers of an inorganic wide band semiconductor. This increases quantum yield and reduces nonradiative recombination, resulting in brighter emission provided that the shell is of a different semiconductor material with a wider bandgap than the core semiconductor material. The higher quantum yield is due to changes in the surface chemistry of the core quantum dot. The surface of nanocrystals that lack a shell has both free (unbonded) electrons, in addition to crystal defects. Both of these characteristics tend to reduce quantum yield by permitting nonradiative electron energy transitions at the surface. A shell reduces opportunities for nonradiative transitions by giving conduction band electrons an increased probability of directly relaxing to the valence band. The shell also neutralizes the effects of many types of surface defects A physician may select specific properties and emission frequencies to selectively regulate polarization in specific sites and for specific results. Thus, the particles are tunable to provide desired properties; for example, they may be size specific, current specific, patient specific, disease specific, activation specific, site specific, etc.

As one example, particles provided throuogut the retinal layers may be selectively regulated to normalize polarization and/or reduce or prevent repolarization, depolarization, and/or hyperpolarization. As another example, selected particles may be administered to selected sites and selectively regulated (e.g., temporally, spacially, activationally, etc.) to result in different effects to fine-tune a desired outcome. More specifically, a patient's progress may be monitored after a slight regulation and, if warranted, further regulation may be administered until a desired outcome is obtained. For example, a patient with muscle tremors may be treated with the inventive method for a duration, extent, activation energy, etc. to selectively repolarize striated muscle cells until a desired effect is reached.

In one embodiment, the particles are mixed into or with a biocompatible fluid. In another embodiment, the particles are in the form of beads or spheres. In another embodiment, the particles are provided as a film. In another embodiment, the particles are drawn and provided as fibers. In any of these embodiments, the particles are provided to a patient by injection to other minimally invasive techniques known to one skilled in the art.

Upon administration, the particles are located intracellularly (within a cell), intercellularly (between cells), or both intracellularly and intercellularly. They may be administered in a number of ways. With respect to the eye, they may be injected through the retina, under the retina superiorly, over the fovea, through the outer plexiform layer down to the fovea, into the vitreous cavity to diffuse through the retina, etc. The procedure permits particles to be located at any site including the macula, that is, the particles may be directly on the macula, directly on the fovea, etc. distinguishing from procedures requiring electrodes to be located beyond the macula or beyond the fovea so as not to block foveal perfusion. The procedure does not require major invasive surgery and is only minimally invasive, in contrast to procedures that involve surgical implantation of an electrode or photovoltaic apparatus. The procedure locates particles diffusively substantially throughout the eye, or selected regions of the eye, in contrast to procedures in which an electrode or other device is located at a single site. Thus, the site of treatment is expanded with the inventive method. In this way, the particles locate within excitable cells, such as the retina, macula, etc. using an ocular example, and also locate between these excitable cells, and are thus dispersed substantially throughout a region of interest. Particles not located as described are handled by the retinal pigment epithelium.

Continuing to use the eye as a non-limiting example, the particles migrate through spaces of retinal cells and distribute through retinal layers, including the RPE. To even more widely disperse particles throughout the retina, they may be sprayed over the retina. In one embodiment, they may be delivered and distributed throughout the retinal layers by a spraying or jetting technique. In this technique, a pressurized fluid (liquid and/or gas) stream is directed toward a targeted body tissue or site, such as retinal tissue, with sufficient energy such that the fluid stream is capable of penetrating the tissue, e.g., the various retinal layers. In applications, the fluid stream, which may be a biologically compatible gas or liquid, acts as a carrier for the particles. By way of example, the spraying technique has been used in cardiac and intravascular applications for affecting localized drug delivery. The teaching of those applications may be applied to the delivery of the particles to the retina. For example, U.S. Pat. No. 6,641,553 which is expressly incorporated by reference herein, discloses pressurizing a fluid carrier having a drug or agent mixed therewith and jetting the mixture into a target tissue.

It will also be appreciated that other agents may be included in the fluid in addition to the particles. These other agents include, but are not limited to, various drugs (antibiotics, anti-angiogenic agents, anti-prostaglandins, anti-neoplastic agents, etc), vectors such as plasmids, viruses, etc. containing genes, oligonucleotides, small interfering RNA (siRNA), etc.

Figure 3:
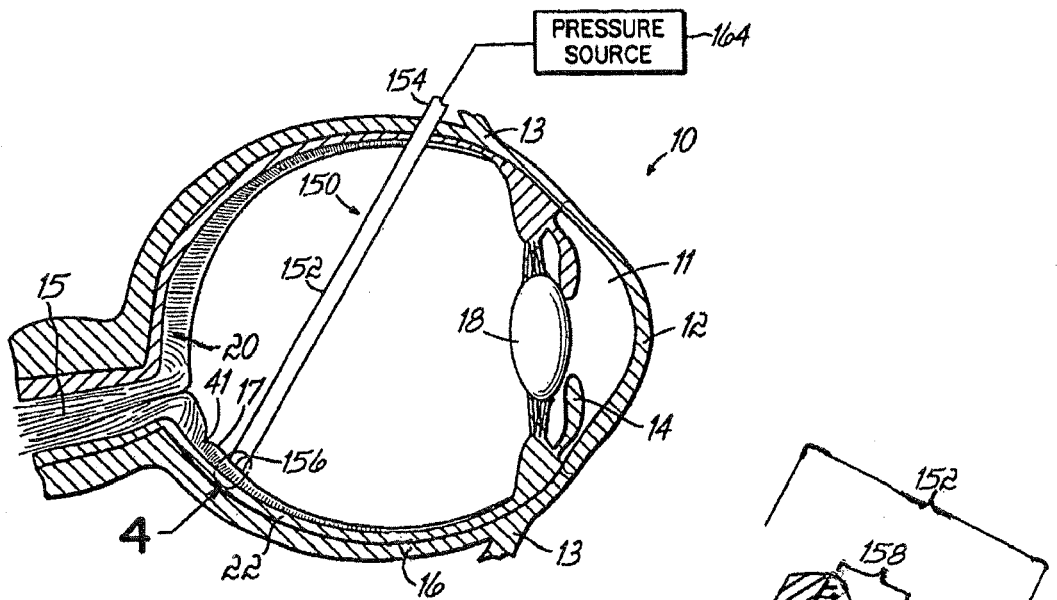
FIG. 3 shows the eye of FIG. 1 with a cannula delivering particles to the retina in accordance with one embodiment of the invention.
Figure 4:
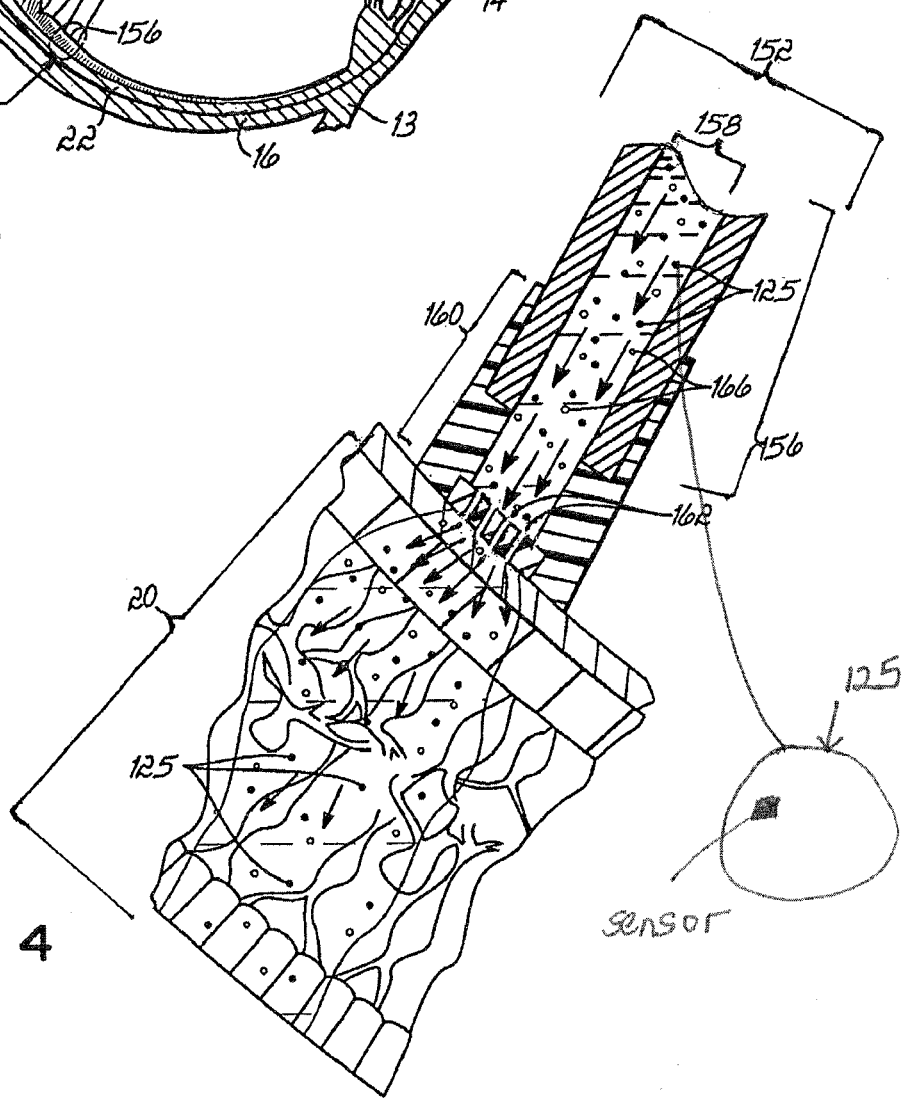
FIG. 4 is an enlarged diagrammatic illustration of the circled area 4 in FIG. 3 showing particles jetting from a cannula and dispersing throughout retinal structures.

As schematically shown in FIGS. 3 and 4, a device 150 for delivering the particles to the retina generally includes an elongated tube or cannula 152 having a proximal end 154 and a distal end 156 and an interior lumen 158 extending between the proximal and distal ends 154, 156. A distal end region 160, which may include a distal end face or a portion of the outer surface of the cannula 152 adjacent the distal end 156, includes a plurality of outlet ports or apertures 162 in fluid communication with the interior lumen 158. The device 150 further includes a pressure control source 164, such as for example a fan or pump, in fluid communication with the lumen 158 and operable for establishing an elevated pressure within the lumen. As known to one skilled in the art, the pressure should be sufficient to effectively disseminate the particles throughout the retina through a spraying or jetting action, but not sufficient to substantially damage retinal tissue. In one embodiment, a pressure may range from 0.0001 psi to 100 psi. The pressurized spraying also assists in distributing particles that disseminate and localize throughout the retinal layers. Localization of the particles permits enhanced control, duration, ease, etc. of stimulating these particles, resulting in enhanced control and effect.

The particles are introduced into the interior lumen 158 from any source, such as from a reservoir chamber, a syringe, etc. (not shown), and are mixed with a carrier fluid 166 such as a biocompatible gas or liquid. As non-limiting examples, air, oxygen, nitrogen, sulfur hexafluoride other perfluorocarbon fluids, etc., alone or in combination, may be used.

The pressurized fluid carrying the particles is regulated for ejection from the outlet ports, and is propelled toward the retina. The diameter of the outlet ports and pressure of the fluid are such as to allow the particles to penetrate the retinal tissue with minimal or no retinal damage. To accomplish a wide distribution of the particles throughout the retinal layers, the pressure may be pulsed to vary the penetration depth of the particles. The cannula may also be rotated or moved to spray or cover a larger area of the retina. Those of ordinary skill in the art will recognize other ways to distribute the particles throughout the retinal layers. As one example, the diameter of the outlet ports may be varied to provide different penetration depths. The outlet port diameters may range from about 0.01 mm to about 1 mm. As another example, the angles of the outlet ports may be varied to provide different spray patterns.

The above-described device may be used in the inventive method to deliver particles to the retina and distribute them substantially throughout the retinal layers, both intracellularly and/or intercellularly. That is, the particles diffusively locate and penetrate the retinal layers.

In one embodiment, an ocular surgeon may remove the vitreous gel, such as by an aspiration probe having vacuum pressure or a cutting probe, and replacing the contents of the vitreous cavity with saline, air, or another biocompatible fluid to facilitate particle penetration. The spraying device is inserted through the incision and into the vitreous cavity. The distal end of the device is positioned on or adjacent the retina, with the surgeon verifying placement using an operating microscope, a slit lamp, or other methods known in the art. Once the distal end of the device is adequately positioned, the pressurized fluid stream carrying the particles is generated and the particles are propelled toward the retina so as to distribute the particles throughout the retinal layers, as previously described. A gas probe may also be inserted into the vitreous cavity, such as by a second incision, to maintain the desired intraocular pressure. In another embodiment, the vitreous gel is not removed and the particles are injected (e.g., using a needle or other type of injection device) without spraying close to the retina, where the particles then diffuse through intercellular spaces of the retina and throughout the eye. Those of ordinary skill in the art will recognize that while the delivery method has been described as using separate aspiration probes, fiber optic probes, and gas probes, a single device that accomplishes delivery of the particles to the retina, removal of the vitreous gel and gas delivery may be used in the inventive method.

Once located at the desired location, the particles are stimulated using an energy source. The energy source may be located external to the eye at either or both the front and back, external to the retina, or on the surface of the retina. Because the retina is transparent, light is able to pass through and hence activate the particles located on and in various retinal tissues, as is subsequently described. The activated particles reset or influence the plasma membrane electrical potential of excitable cells, resulting in a desired response in membrane polarity. As previously described, this may take the form of normalized polarization, repolarization, enhanced polarization (i.e., stimulation), or reduced polarization (i.e., calming), etc.

In one embodiment, the particles are delivered into the eye when the vitreous gel is removed and replaced with saline and the internal limiting membrane (ILM) is removed. In one embodiment, the internal limiting membrane is removed to permit particle dissemination within the retina and throughout retinal intracellular spaces. This enhances diffusion of particles in the retina so that, by fluid flow, particles can then disseminate and penetrate retinal layers. Particles may adhere to the outer cellular membrane and/or may enter retinal cells. The particle size and/or spraying pressure, location, formulation may be altered to aid in selectivity. Particle penetration may be limited by the external limiting membrane (ELM), which may act as a semi-barrier to retinal transport. Excess particles may be removed as a part of the normal phagocytosis process (e.g., by glial cells). Ganglial cells in the eye, responsible for visual processing (discerning motion, depth, fine shapes, textures, colors), have less active phagocytosis mechanisms, so treatment of these cells may be affected by spraying to minimize excess distribution of particles.

Repolarization of cell membranes in a first location may have beneficial effects on polarization of cell membranes in second and subsequent locations. Due to propagation of electrical stimuli, a wave of electrical distribution is disseminated throughout the retina, for example, along a glial cell network. Because the glial cells assist in maintaining electrical balance, propagation also stabilizes polarization of adjacent cells.

It will be appreciated from the above description that stimulation of the entire retina may be achieved, rather than stimulation of a portion of the retina in proximity to a fixed electrode. This achieves substantially uniform repolarization, minimizing or preventing areas of hyper- and/or hypo-polarization, which assist in functional regeneration of glial cells.

In one embodiment, an ocular surgeon may stimulate the particles with an external light source, by ambient light, by ultrasound radiation, or by other mechanisms known to one skilled in the art. The particles facilitate, enhance, or boost a biological cell's regulation of its polarity, with adjacent cells capable of being stimulated due to the glial stimulus-propagating network.

Other variations or embodiments of the invention will also be apparent to one of ordinary skill in the art from the above description. As one example, other forms, routes, and sites of administration are contemplated. As another example, the invention may be used in patients who have experienced ocular trauma, retinal degeneration, ischemia, inflammation, etc. As another example, the particles may include sensing devices for qualitative and/or quantitative chemistry or other determinations. For example, the particles may include sensors or other detection means for glucose, oxygen, glycosylated hemoglobin, proteins including but limited to enzymes, pressure, indicators for retinal degenerative disease, etc. Thus, the forgoing embodiments are not to be construed as limiting the scope of this invention.

What is claimed is:

1. A method to controllably regulate plasma membrane polarization of a functional retinal cell excitable by light but having abnormal membrane polarization, the method comprising the steps of
   administering a plurality of quantum dots mixed into or with a biocompatible fluid to an eye of a patient in need thereof, the eye having a light-excitable functional retinal cell having abnormal membrane polarization,
   applying light to the quantum dots under conditions sufficient to controllably activate the quantum dots to controllably regulate the plasma membrane polarization of the light-excitable retinal cell by the activated quantum dots, and
   monitoring the altered plasma membrane polarization for at least one of a normal polarization state, a repolarized state, a hyperpolarized state, or a hypopolarized state.

2. The method of claim 1 further comprising selectively regulating polarization in areas of the cell bound by occluding junctions by regulating the site of exposure.

3. The method of claim 1 wherein the patient in need thereof has a degenerative disease of the retinal cell.

4. The method of claim 1 wherein at least one of the time of exposure or intensity of exposure of the light is increased from an initial time or intensity so that the regulated plasma membrane polarization of the retinal cell is propagated to at least a second retinal cell.

5. The method of claim 1 wherein the administering step further comprises administering sensor-containing quantum dots sensitive to at least one physiologic parameter of a patient, and the monitoring step further comprises monitoring data from the sensors to further provide at least one physiologic parameter in the patient.

6. The method of claim 1 wherein the light applied is at least one of ambient light, ultraviolet light, visible light, or infrared light.

7. A method to controllably regulate plasma membrane polarization of at least one functional abnormally polarized retinal cone or rod cell excitable by light, the method comprising the steps of
   providing a plurality of quantum dots to a vitreous cavity of an eye of a patient in need thereof, the eye also having a plurality of biological cells comprising a retina, the quantum dots provided in a fluid sufficient to diffusively disseminate the quantum dots substantially throughout the retinal cells,
   applying light to the quantum dots under conditions sufficient to controllably activate the quantum dots to controllably regulate the plasma membrane polarization of the functional abnormally polarized light-excitable retinal cone or rod cell by the activated quantum dots, and
   monitoring the altered plasma membrane polarization for at least one of a normal polarization state, a repolarized state, a hyperpolarized state, or a hypopolarized state.

8. The method of claim 7 wherein the quantum dots are provided to the vitreous cavity by spraying.

9. The method of claim 7 further comprising a preliminary step of substantially removing vitreous fluid from the vitreous cavity and then performing the method where vitreous fluid is substantially absent from the vitreous cavity.

10. The method of either of claim 1 or claim 7 wherein the desired regulation alleviates a retinal pathology.

11. The method of either claim 1 or claim 7 further comprising spatially regulating the quantum dots in a specific area of the retina.

12. The method of either claim 1 or claim 7 occuring in the absence of an action potential from the activated quantum dots.

* * * * *